United States Patent
Cade et al.

(10) Patent No.: US 7,005,562 B2
(45) Date of Patent: Feb. 28, 2006

(54) SAR AND PATHOGEN-INDUCIBLE PROMOTER

(75) Inventors: Rebecca M. Cade, Durham, NC (US); Robert A. Dietrich, Durham, NC (US)

(73) Assignee: Syngenta Participations AG, Schwarzwaldallee (CH)

( * ) Notice: Subject to any disclaimer, the term of this patent is extended or adjusted under 35 U.S.C. 154(b) by 209 days.

(21) Appl. No.: 10/760,752

(22) Filed: Jan. 20, 2004

(65) Prior Publication Data

US 2004/0248303 A1 Dec. 9, 2004

Related U.S. Application Data

(62) Division of application No. 09/733,685, filed on Dec. 8, 2000, now Pat. No. 6,706,952.

(60) Provisional application No. 60/171,008, filed on Dec. 15, 1999, provisional application No. 60/175,519, filed on Jan. 11, 2000.

(51) Int. Cl.
*C12N 15/82* (2006.01)
*C12N 15/11* (2006.01)
*A01H 5/00* (2006.01)
*A01H 5/10* (2006.01)

(52) U.S. Cl. .................. 800/298; 536/24.1; 435/320.1; 435/419; 424/93.2

(58) Field of Classification Search ..................... None
See application file for complete search history.

(56) References Cited

PUBLICATIONS

Zhong et al, 1999, Genbank Accession No. AC005142.*
Huang et al, 1999, Genbank Accession No. AF071527.*

* cited by examiner

*Primary Examiner*—Anne Kubelik
(74) *Attorney, Agent, or Firm*—Syngenta Participations AG

(57) ABSTRACT

The *Arabidopsis* NI16 gene was isolated in a yeast 2-hybrid screen via its interaction with the NIM1 protein and encodes a protein involved in the regulation of SAR gene expression in plants. NI16 is strongly induced in NIM1-overexpressing plants treated with benzo(1,2,3)thiadiazole-7-carbothioic acid S-methyl ester (BTH). The nucleic acid sequence of the *Arabidopsis* NI16 promoter is disclosed herein.

7 Claims, No Drawings

SAR AND PATHOGEN-INDUCIBLE PROMOTER

This application is a divisional of U.S. application Ser. No. 09/733,685, filed Dec. 8, 2000, now U.S. Pat. No. 6,706,952, which claims the benefit of U.S. Provisional Application No. 60/171,008, filed Dec. 15, 1999, and U.S. Provisional Application No. 60/175,519, filed Jan. 11, 2000, all of which are incorporated herein by reference in their entirety.

FIELD OF THE INVENTION

The present invention relates to broad-spectrum disease resistance in plants, including the phenomenon of systemic acquired resistance (SAR). More particularly, the present invention relates to the identification, isolation and characterization of genes encoding proteins that are involved in the regulation of SAR gene expression in plants.

BACKGROUND OF THE INVENTION

Plants are constantly challenged by a wide variety of pathogenic organisms including viruses, bacteria, fungi, and nematodes. Crop plants are particularly vulnerable because they are usually grown as genetically-uniform monocultures; when disease strikes, losses can be severe. However, most plants have their own innate mechanisms of defense against pathogenic organisms. Natural variation for resistance to plant pathogens has been identified by plant breeders and pathologists and bred into many crop plants. These natural disease resistance genes often provide high levels of resistance to or immunity against pathogens.

Systemic acquired resistance (SAR) is one component of the complex system plants use to defend themselves from pathogens (Hunt and Ryals, 1996; Ryals et al., 1996). See also, U.S. Pat. No. 5,614,395. SAR is a particularly important aspect of plant-pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., 1993; Delaney et al., 1994; Delaney et al., 1995; Delaney, 1997; Bi et al., 1995; Mauch-Mani and Slusarenko, 1996). These observations indicate that the SAR signal transduction pathway is critical for maintaining plant health.

Conceptually, the SAR response can be divided into two phases. In the initiation phase, a pathogen infection is recognized, and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state, and disease resistance is maintained (Ryals et al., 1996).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot induce either SAR gene expression or disease resistance (Gaffney et al., 1993; Delaney et al., 1994; Mauch-Mani and Slusarenko, 1996; Maher et al., 1994; Pallas et al., 1996). Although it has been suggested that SA might serve as the systemic signal, this is currently controversial and, to date, all that is known for certain is that if SA cannot accumulate, then SAR signal transduction is blocked (Pallas et al., 1996; Shulaev et al., 1995; Vernooij et al., 1994).

Recently, *Arabidopsis* has emerged as a model system to study SAR (Uknes et al., 1992; Uknes et al., 1993; Cameron et al., 1994; Mauch-Mani and Slusarenko, 1994; Dempsey and Klessig, 1995). It has been demonstrated that SAR can be activated in *Arabidopsis* by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., 1995; Lawton et al., 1996). Following treatment with either INA or BTH or pathogen infection, at least three pathogenesis-related (PR) protein genes, namely, PR-1, PR-2, and PR-5 are coordinately induced concomitant with the onset of resistance (Uknes et al., 1992, 1993). In tobacco, the best characterized species, treatment with a pathogen or an immunization compound induces the expression of at least nine sets of genes (Ward et al., 1991). Transgenic disease-resistant plants have been created by transforming plants with various SAR genes (U.S. Pat. No. 5,614,395).

A number of *Arabidopsis* mutants have been isolated that have modified SAR signal transduction (Delaney, 1997) The first of these mutants are the so-called lsd (lesions simulating disease) mutants and acd2 (accelerated cell death) (Dietrich et al., 1994; Greenberg et al., 1994). These mutants all have some degree of spontaneous necrotic lesion formation on their leaves, elevated levels of SA, mRNA accumulation for the SAR genes, and significantly enhanced disease resistance. At least seven different lsd mutants have been isolated and characterized (Dietrich et al., 1994; Weymann et al., 1995). Another interesting class of mutants are cim (constitutive immunity) mutants (Lawton et al., 1993). See also, U.S. Pat. No. 5,792,904 and International PCT Application WO 94/16077. Like lsd mutants and acd2, cim mutants have elevated SA and SAR gene expression and resistance, but in contrast to lsd or acd2, do not display detectable lesions on their leaves. cpr1 (constitutive expresser of PR genes) may be a type of cim mutant; however, because the presence of microscopic lesions on the leaves of cpr1 has not been ruled out, cpr1 might be a type of lsd mutant (Bowling et al., 1994).

Mutants have also been isolated that are blocked in SAR signaling. ndr1 (non-race-specific disease resistance) is a mutant that allows growth of both *Pseudomonas syringae* containing various avirulence genes and also normally avirulent isolates of *Peronospora parasitica* (Century et al., 1995). Apparently this mutant is blocked early in SAR signaling. npr1 (nonexpresser of PR genes) is a mutant that cannot induce expression of the SAR signaling pathway following INA treatment (Cao et al., 1994). eds (enhanced disease susceptibility) mutants have been isolated based on their ability to support bacterial infection following inoculation of a low bacterial concentration (Glazebrook et al., 1996; Parker et al., 1996). Certain eds mutants are phenotypically very similar to npr1, and, recently, eds5 and eds53 have been shown to be allelic to npr1 (Glazebrook et al., 1996). nim1 (noninducible immunity) is a mutant that supports *P. parasitica* (i.e., causal agent of downy mildew disease) growth following INA treatment (Delaney et al., 1995; U.S. Pat. No. 5,792,904). Although nim1 can accumulate SA following pathogen infection, it cannot induce SAR gene expression or disease resistance, suggesting that the mutation blocks the pathway downstream of SA. nim1 is also impaired in its ability to respond to INA or BTH, suggesting that the block exists downstream of the action of these chemicals (Delaney et al., 1995; Lawton et al., 1996).

Allelic *Arabidopsis* genes have been isolated and characterized, mutants of which are responsible for the nim1 and npr1 phenotypes, respectively (Ryals et al., 1997; Cao et al., 1997). The wild-type NIM1 gene product is involved in the signal transduction cascade leading to both SAR and gene-for-gene disease resistance in *Arabidopsis* (Ryals et al., 1997). Ryals et al., 1997 also report the isolation of five additional alleles of nim1 that show a range of phenotypes from weakly impaired in chemically induced PR-1 gene expression and fungal resistance to very strongly blocked. Transformation of the wild-type NPR1 gene into npr1 mutants not only complemented the mutations, restoring the responsiveness of SAR induction with respect to PR-gene expression and disease resistance, but also rendered the transgenic plants more resistant to infection by *P. syringae* in the absence of SAR induction (Cao et al., 1997). WO 98/06748 describes the isolation of NPR1 from *Arabidopsis* and a homologue from *Nicotiana glutinosa*. See also, WO 97/49822, WO 98/26082, and WO 98/29537.

Despite much research and the use of sophisticated and intensive crop protection measures, including genetic transformation of plants, losses due to disease remain in the billions of dollars annually. Therefore, there is a continuing need to develop new crop protection measures based on the ever-increasing understanding of the genetic basis for disease resistance in plants. In particular, there is a long-felt need for the identification, isolation, and characterization of more genes involved in the signal transduction cascade leading to systemic acquired resistance in plants.

SUMMARY OF THE INVENTION

The present invention addresses the aforementioned long-felt needs by using the *Arabidopsis* NIM1 gene as bait in a two-hybrid screen to identify plant proteins that interact with the NIM1 protein. The novel NI16 and NI19 genes are obtainable by this screen. Homologues of the NI16 gene are obtainable by PCR amplification of total cellular DNA from other plants such as potato and tomato. The NI16 gene is rapidly induced following treatment with salicylic acid (SA) and benzo(1,2,3)thiadiazole-7-carbothioic acid S-methyl ester (BTH), as well as by pathogen inoculation. The NI16 gene is also induced in NIM1-overexpressing plants treated with BTH. Transgenic expression of the NI16 gene results in elevated levels of the pathogenesis-related (PR) protein PR-1. The amount of PR-1 induced correlates with the amount of NI16 present, i.e., transgenic plants with the highest expression of NI16 have the highest levels of PR-1. It is believed that NI16 is a necessary component of the SAR response, and that overexpression of NI16 activates a subset of the response. PR-1 is also elevated in nahG and nim1-1 plants overexpressing NI16, which is significant because both nim1 and nahG plants are normally deficient in their ability to induce PR-1 in response to pathogens. Thus, the NI16 gene encodes a protein involved in the regulation of SAR gene expression in plants. The NI16 gene can be expressed in transgenic plants, either alone or in combination with the NIM 1 protein, to enhance expression of SAR genes such as PR-1.

In particular, the present invention is directed to an isolated nucleic acid molecule comprising a sequence that encodes the amino acid sequence of SEQ ID NO:2, SEQ ID NO:5, SEQ ID NO:7, or SEQ ID NO:23.

The present invention is further directed to an isolated nucleic acid molecule comprising the coding region of SEQ ID NO:1, SEQ ID NO:3, SEQ ID NO:4, SEQ ID NO:6, or SEQ ID NO:22.

The present invention is also directed to an isolated nucleic acid molecule comprising a sequence that encodes a protein involved in the signal transduction cascade leading to systemic acquired resistance in plants, wherein said sequence comprises a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of the coding region of SEQ ID NO:1, SEQ ID NO:3, SEQ ID NO:4, SEQ ID NO:6, or SEQ ID NO:22.

The present invention is further directed to an isolated nucleic acid molecule comprising a nucleotide sequence that encodes a protein involved in the signal transduction cascade leading to systemic acquired resistance in plants, wherein said nucleotide sequence can be amplified from total cellular DNA from a plant using the polymerase chain reaction with the primers shown as SEQ ID NO:20 and SEQ ID NO:21.

The present invention also encompasses a chimeric gene comprising a promoter active in plants operatively linked to a coding sequence of the present invention, a recombinant vector comprising such a chimeric gene, wherein the vector is capable of being stably transformed into a host, as well as a host stably transformed with such a vector. Preferably, the host is a plant such as one of the following agronomically important crops: rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane.

In another aspect, the present invention provides the nucleic acid sequence of the NI16 promoter, an example of which is presented in SEQ ID NO:3. A preferred embodiment of the NI16 promoter comprises the region upstream of nucleotide number 863 of SEQ ID NO:3. In addition, the present invention encompasses chimeric genes comprising the NI16 promoter operatively linked to a coding sequence of a gene of interest, wherein the NI16 promoter regulates transcription of the coding sequence in the presence of chemical regulators. In a preferred embodiment, the coding sequence encodes an enzyme, such as an assayable marker, whereby expression of the marker can be observed in assays for chemical induction of the chimeric gene. In related aspects, the present invention also embodies a recombinant vector, such as a plasmid, comprising the aforementioned chimeric gene, as well as a plant or plant tissue stably transformed with such a chimeric gene.

BRIEF DESCRIPTION OF THE SEQUENCES IN THE SEQUENCE LISTING

SEQ ID NO: 1—Full length cDNA sequence of the *Arabidopsis thaliana* NI16 gene.
SEQ ID NO:2—Amino acid sequence of the NI16 protein encoded by SEQ ID NO: 1.
SEQ ID NO:3—Genomic DNA sequence of the *Arabidopsis thaliana* NI16 gene region, including the 5' upstream promoter sequence.
SEQ ID NO:4—Full length cDNA sequence of the potato NI16 homologue.

SEQ ID NO:5—Potato NI16 amino acid sequence encoded by SEQ ID NO:4.
SEQ ID NO:6—Partial cDNA sequence of the tomato NI16 homologue.
SEQ ID NO:7—Tomato NI16 amino acid sequence encoded by SEQ ID NO:6.
SEQ ID NO:8—Amino acid sequence encoded by soybean EST A1495102.
SEQ ID NO:9—Amino acid sequence encoded by soybean EST A1461039.
SEQ ID NO:10—Amino acid sequence encoded by tobacco G8-1 gene.
SEQ ID NO:11—Primer NIM5'RI
SEQ ID NO:12—Primer NIM3'SalI
SEQ ID NO:13—Primer NIMtrunc3'NcoI
SEQ ID NO:14—Primer NIMloop5'RI
SEQ ID NO:15—Primer 16GSP1
SEQ ID NO:16—Primer 16GSP2
SEQ ID NO:17—Primer 16GSP3
SEQ ID NO:18—Primer 16F
SEQ ID NO:19—Primer 16R
SEQ ID NO:20—Primer NI16-DegF
SEQ ID NO:21—Primer NI16-DegR
SEQ ID NO:22—Genomic sequence of the *Arabidopsis thaliana* NI19 gene.
SEQ ID NO:23—Amino acid sequence of the NI19 protein encoded by SEQ ID NO:22.

Definitions

In describing the present invention, the following terms will be employed, and are intended to be defined as indicated below.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding Sequence: a nucleic acid sequence that is transcribed into RNA such as mRNA, rRNA, tRNA, snRNA, sense RNA or antisense RNA. Preferably the RNA is then translated in an organism to produce a protein.

Complementary: refers to two nucleotide sequences that comprise antiparallel nucleotide sequences capable of pairing with one another upon formation of hydrogen bonds between the complementary base residues in the antiparallel nucleotide sequences.

Expression: refers to the transcription and/or translation of an endogenous gene or a transgene in plants. In the case of antisense constructs, for example, expression may refer to the transcription of the antisense DNA only.

Expression Cassette: A nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

Gene: A defined region that is located within a genome and that, besides the aforementioned coding nucleic acid sequence, comprises other, primarily regulatory, nucleic acid sequences responsible for the control of expression, i.e., transcription and translation of the coding portion. A gene may also comprise other 5' and 3' untranslated sequences and termination sequences. Further elements that may be present are, for example, introns.

Heterologous DNA Sequence: The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also includes non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

Homologous DNA Sequence: A DNA sequence naturally associated with a host cell into which it is introduced.

Isocoding: A nucleic acid sequence is isocoding with a reference nucleic acid sequence when the nucleic acid sequence encodes a polypeptide having the same amino acid sequence as the polypeptide encoded by the reference nucleic acid sequence.

Isolated: In the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

Minimal Promoter: a promoter element, particularly a TATA element, that is inactive or has greatly reduced promoter activity in the absence of upstream activation. In the presence of a suitable transcription factor, a minimal promoter functions to permit transcription.

Native: refers to a gene that is present in the genome of an untransformed cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

NI16: Gene involved in the SAR signal transduction cascade that interacts with the NIM1 protein.

NIM1: Gene described in Ryals et al., 1997, which is involved in the SAR signal transduction cascade.

NIM1: Protein encoded by the NIM1 gene.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" may also be used interchangeably with gene, cDNA, and mRNA encoded by a gene. In the context of the present invention, the nucleic acid molecule is preferably a segment of DNA. Nucleotides are indicated by their bases by the following standard abbreviations: adenine (A), cytosine (C), thymine (T), and guanine (G).

ORF: Open Reading Frame.

Plant: Any whole plant.

Plant Cell: Structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

Plant Cell Culture: Cultures of plant units such as, for example, protoplasts, cell culture cells, cells in plant tissues, pollen, pollen tubes, ovules, embryo sacs, zygotes and embryos at various stages of development.

Plant Material: Refers to leaves, stems, roots, flowers or flower parts, fruits, pollen, egg cells, zygotes, seeds, cuttings, cell or tissue cultures, or any other part or product of a plant.

Plant Organ: A distinct and visibly structured and differentiated part of a plant such as a root, stem, leaf, flower bud, or embryo.

Plant tissue: A group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

Promoter: An untranslated DNA sequence upstream of the coding region that contains the binding site for RNA polymerase II and initiates transcription of the DNA. The promoter region may also include other elements that act as regulators of gene expression.

Protoplast: An isolated plant cell without a cell wall or with only parts of the cell wall.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

Recombinant DNA molecule: a combination of DNA molecules that are joined together using recombinant DNA technology.

Regulatory Elements: Sequences involved in controlling the expression of a nucleotide sequence. Regulatory elements comprise a promoter operably linked to the nucleotide sequence of interest and termination signals. They also typically encompass sequences required for proper translation of the nucleotide sequence.

Selectable marker gene: a gene whose expression in a plant cell gives the cell a selective advantage. The selective advantage possessed by the cells transformed with the selectable marker gene may be due to their ability to grow in the presence of a negative selective agent, such as an antibiotic or a herbicide, compared to the growth of non-transformed cells. The selective advantage possessed by the transformed cells, compared to non-transformed cells, may also be due to their enhanced or novel capacity to utilize an added compound as a nutrient, growth factor or energy source. Selectable marker gene also refers to a gene or a combination of genes whose expression in a plant cell gives the cell both, a negative and a positive selective advantage.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

Substantially identical: the phrase "substantially identical," in the context of two nucleic acid or protein sequences, refers to two or more sequences or subsequences that have at least 60%, preferably 80%, more preferably 90–95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

A "subsequence" refers to a sequence of nucleic acids or amino acids that comprise a part of a longer sequence of nucleic acids or amino acids (e.g., protein) respectively.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

A "specific binding affinity" between two molecules, for example, a ligand and a receptor, means a preferential binding of one molecule for another in a mixture of molecules. The binding of the molecules can be considered specific if the binding affinity is about $1 \times 10^4$ M-1 to about $1 \times 10^6$ $M^{-1}$ or greater.

Transformation: a process for introducing heterologous DNA into a host cell or organism.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Deposit Information

The following material has been deposited with the Agricultural Research Service, Patent Culture Collection (NRRL), 1815 North University Street, Peoria, Ill. 61604, USA, under the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
|-------|------------------|-----------------|
| pRC25 | NRRL B-30239 | Jan. 7, 2000 |

DETAILED DESCRIPTION OF THE INVENTION

The *Arabidopsis* NIM1 gene (Ryals et al., 1997) is used as a bait in a yeast two-hybrid screen to isolate the novel NIM 1 interactors NI16 and NI19. The NI16 gene is rapidly induced following treatment with salicylic acid (SA) and benzo(1,2,3)thiadiazole-7-carbothioic acid S-methyl ester (BTH), as well as by pathogen inoculation. The NI16 gene is also induced in NIM1-overexpressing plants treated with BTH. The NI16 gene sequence contains regions of high homology to the tobacco G8-1 gene, which is induced rapidly following treatment with salicylic acid, and which is responsive to very low concentrations of salicylate.

A full length *Arabidopsis* NI16 cDNA is determined by 5' RACE kit and encodes a protein of 122 amino acids. In addition, a genomic copy of *Arabidopsis* NI16 is cloned from a genomic library. The genomic clone also contains the NI16 5' upstream promoter region, which includes several promoter elements in the region adjacent to the NI16 genomic coding region. These promoter elements include: a tandem CaMV AS1 motif, which is known to be SA inducible (Terzaghi and Cashmore, 1995); a tandem TCA1 motif, which is another common SA inducible element (Goldsbrough et al., 1993); a MYCATR22 element, which is a binding site for MCY (rd22BPI) in *Arabidopsis* dehydration-responsive gene rd22 (ABA-induction); a PAL BOX, which is one of three putative cis-acting elements of the phenylalanine ammonia-lyase family in parsley; and a HEX-AMERAT4 element, which is a hexamer motif of the *Arabidopsis* histone H4 promoter. Because the NI16 gene is rapidly induced following treatment with the SAR inducers SA and BTH, it is predicted that the NI16 promoter is inducible by a full range of known SAR-inducers and can therefore be used for the same purposes as described for the tobacco PR-1a promoter in U.S. Pat. No. 5,614,395 and for the *Arabidopsis* PR-1 promoter in WO 98/03536.

NI16 and NI19 gene sequences according to the invention can be isolated using the techniques described in the examples below, or by PCR using the NI16 sequences (SEQ ID NO:1 or SEQ ID NO:3) or NI19 sequence (SEQ ID NO:22) set forth in the sequence listing as the basis for constructing PCR primers. For example, oligonucleotides corresponding to the sequence of approximately the first and last 20–25 consecutive nucleotides of the NI16 coding sequence or their complements (e.g., SEQ ID NO:20 and SEQ ID NO:21) can be used as PCR primers to amplify a NI16 gene sequence directly from a cDNA or genomic library from a source plant such as *Arabidopsis thaliana*, potato or tomato. Thus, the NI16 and NI19 gene sequences set forth in the sequence listing, as well as homologous NI16 and NI19 gene sequences from additional plants, can likewise be amplified by PCR from cDNA and genomic libraries.

Transgenic expression of the NI16 gene results in constitutive expression of PR-1. Hence, the NI16 gene encodes a protein involved in the regulation of SAR gene expression.

A NI16 or NI19 coding sequence of the present invention may be inserted into an expression cassette designed for plants to construct a chimeric gene according to the invention using standard genetic engineering techniques. The choice of specific regulatory sequences such as promoter, signal sequence, 5' and 3' untranslated sequences, and enhancer appropriate for the achieving the desired pattern and level of expression in the chosen plant host is within the level of skill of the routineer in the art. The resultant molecule, containing the individual elements linked in proper reading frame, may be inserted into a vector capable of being transformed into a host plant cell.

Examples of promoters capable of functioning in plants or plant cells (i.e., those capable of driving expression of associated coding sequences such as those coding for the NI16 or NI19 protein in plant cells) include the *Arabidopsis* and maize ubiquitin promoters; cauliflower mosaic virus (CaMV) 19S or 35S promoters and CaMV double promoters; rice actin promoters; PR-1 promoters from tobacco, *Arabidopsis*, or maize; nopaline synthase promoters; small subunit of ribulose bisphosphate carboxylase (ssu-RUBISCO) promoters, and the like. Especially preferred is the *Arabidopsis* ubiquitin promoter. The promoters themselves may be modified to manipulate promoter strength to increase expression of the associated coding sequence in accordance with art-recognized procedures. Preferred promoters for use with the present invention are those that confer high level constitutive expression.

Signal or transit peptides may be fused to the NI16 coding sequence in the chimeric DNA constructs of the invention to direct transport of the expressed protein to the desired site of action. Examples of signal peptides include those natively linked to the plant pathogenesis-related proteins, e.g. PR-1, PR-2, and the like. See, e.g., Payne et al., 1988. Examples of transit peptides include the chloroplast transit peptides such as those described in Von Heijne et al. (1991), Mazur et al. (1987), and Vorst et al. (1988); and mitochondrial transit peptides such as those described in Boutry et al. (1987). Also included are sequences that result in localization of the encoded protein to various cellular compartments such as the vacuole. See, for example, Neuhaus et al. (1991) and Chrispeels (1991).

The chimeric DNA construct(s) of the invention may contain multiple copies of a promoter or multiple copies of a NI16 or NI19 coding sequence of the present invention. In addition, the construct(s) may include coding sequences for markers and coding sequences for other peptides such as signal or transit peptides, each in proper reading frame with the other functional elements in the DNA molecule. The preparation of such constructs are within the ordinary level of skill in the art.

Useful markers include peptides providing herbicide, antibiotic or drug resistance, such as, for example, resistance to protoporphyrinogen oxidase inhibitors, hygromycin, kanamycin, G418, gentamycin, lincomycin, methotrexate, glyphosate, phosphinothricin, or the like. These markers can be used to select cells transformed with the chimeric DNA constructs of the invention from untransformed cells. Other useful markers are peptidic enzymes which can be easily detected by a visible reaction, for example a color reaction, for example luciferase, β-glucuronidase, or β-galactosidase.

Chimeric genes designed for plant expression such as those described herein can be introduced into the plant cell in a number of art-recognized ways. Those skilled in the art will appreciate that the choice of method might depend on the type of plant (i.e. monocot or dicot) and/or organelle (i.e. nucleus, chloroplast, mitochondria) targeted for transformation. Suitable methods of transforming plant cells include microinjection (Crossway et al., 1986), electroporation (Riggs et al., 1986), *Agrobacterium* mediated transformation (Hinchee et al., 1988; Ishida et al., 1996), direct gene transfer (Paszkowski et al., 1984; Hayashimoto et al., 1990), and ballistic particle acceleration using devices available from Agracetus, Inc., Madison, Wis. and Dupont, Inc., Wilmington, Del. (see, for example, U.S. Pat. No. 4,945, 050; and McCabe et al., 1988). See also, Weissinger et al. (1988); Sanford et al. (1987) (onion); Christou et al. (1988) (soybean); McCabe et al. (1988) (soybean); Datta et al. (1990) (rice); Klein et al. (1988) (maize); Klein et al. (1988) (maize); Klein et al. (1988) (maize); Fromm et al. (1990); and Gordon-Kamm et al. (1990) (maize); Svab et al. (1990) (tobacco chloroplasts); Gordon-Kamm et al. (1993) (maize); Shimamoto et al. (1989) (rice); Christou et al. (1991) (rice); Datta et al. (1990) (rice); European Patent Application EP 0 332 581 (orchardgrass and other Pooideae); Vasil et al. (1993) (wheat); Weeks et al. (1993) (wheat); Wan et al. (1994) (barley); Jahne et al. (1994) (barley); Umbeck et al. (1987) (cotton); Casas et al. (1993) (sorghum); Somers et al. (1992) (oats); Torbert et al. (1995) (oats); Weeks et al., (1993) (wheat); WO 94/13822 (wheat); and Nehra et al. (1994) (wheat). A particularly preferred set of embodiments for the introduction of recombinant DNA molecules into maize by microprojectile bombardment can be found in Koziel et al. (1993); Hill et al. (1995) and Koziel et al. (1996). An additional preferred embodiment is the protoplast transformation method for maize as disclosed in EP 0 292 435.

Once a chimeric gene comprising a NI16 or NI19 coding sequence has been transformed into a particular plant species, it may be propagated in that species or moved into other varieties of the same species, particularly including commercial varieties, using traditional breeding techniques. Preferred plants of the invention include gymnosperms, monocots, and dicots, especially agronomically important crop plants, such as rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. The genetic properties engineered into the transgenic seeds and plants described above are passed on by sexual reproduction and can thus be maintained and propagated in progeny plants.

EXAMPLES

The invention is illustrated in further detail by the following detailed procedures, preparations, and examples. The examples are for illustration only, and are not to be construed as limiting the scope of the present invention. Standard recombinant DNA and molecular cloning techniques used here are well known in the art and are described by Sambrook, et al., 1989; by T. J. Silhavy, M. L. Berman, and L. W. Enquist, 1984; and by Ausubel, F. M. et al., 1987.

I. Isolation of NIM1 Interactors

Example 1

NIM1 Two-Hybrid Screen

The *Arabidopsis* NIM1 gene (Ryals et al., 1997) is used as a bait in a yeast two-hybrid screen. The screen used is the LexA-based version of the two hybrid screen originally developed by Fields and Song (1989) and later modified by Gyuris et al. (1993). A full length NIM1 gene sequence is cloned into the bait plasmid pEG202 (Gyuris et al., 1993) as a fusion with the LexA DNA binding domain using a PCR product (primers NIM5'RI and NIM3'SalI, see Table 1 below). Another bait (NIM450) is constructed using a nucleotide sequence encoding the first 450 amino acids of the NIM1 protein (Ryals et al., 1997) with the primers NIM 5'RI and NIMtrunc NCOI3'. A third bait containing only the C-terminal portion of the NIM1 gene encoding amino acids 366–594 of the NIM1 protein (Ryals et al., 1997) is cloned using the primers NIMloop5'RI and NIM 3'SalI. These baits are transformed into yeast strain EGY188, which contains a low sensitivity LexA operator fused to the Leu2 gene, and appropriate tests are performed to determine whether the NIM1 fusion proteins intrinsically activate expression of the yeast reporter genes. A yeast expression library (obtained from Jeff Dangl, UNC-Chapel Hill) is constructed in plasmid pJG4-5 using RNA from *Arabidopsis* leaves infected with *Pseudomonas syringae*. This library encodes fusion proteins of expressed *Arabidopsis* genes and the B42 transcriptional activation domain. The library is transformed in combination with one of the three NIM1 baits above and a plasmid containing 2 LexA operators fused to LacZ as a secondary reporter. Approximately $10^6$ transformants are analyzed in screens with each bait, and individual clones that activate both the Leu2 and LacZ reporters are isolated and sequenced by standard procedures. The most frequently isolated clone (NI16) is found 25 times with the NIM366–594 bait and 12 times with the full-length bait. The NI16 clone does not interact with the NIM450 bait.

A full-length NI16 cDNA is determined using a 5' RACE kit from BRL Life Technologies. cDNA primer 16GSP1 is used for CDNA synthesis. Then, following a TdT tailing reaction, primer 16GSP2 is used in combination with an abridged anchor primer provided by the manufacturer to amplify the cDNA product by PCR. A third primer, 16GSP3, is used as a PCR control in combination with the GSP2 primer. A cDNA fragment is amplified and cloned into the pCR2.1 vector (Clonetech) and sequenced.

The full-length *Arabidopsis* NI16 cDNA sequence is shown as SEQ ID NO:1, and the encoded 122-amino acid protein sequence is shown as SEQ ID NO:2. The NI16 gene sequence contains regions of high homology to the tobacco G8-1 gene, which is induced rapidly following treatment with salicylic acid, and which is responsive to very low concentrations of salicylate (Horvath et al., 1996).

Example 2

Induction of NI16 mRNA

1. Salicylic Acid and BTH Induce NI16 mRNA

RNA is prepared from 4 week old Wassilewskija (WS-O) plants, that are either sprayed with water, a 5 mM solution of sodium salicylate (SA), or a 300 μm solution of benzo-(1,2,3)-thiadiazole-7-carbothioic acid S-methyl ester (BTH). SA and BTH both have been demonstrated to activate SAR in *Arabidopsis* and to induce pathogenesis related (PR) gene expression by Ward et al. (1991) and Lawton et al. (1996). RNA extractions and RNA blot hybridizations are performed as described previously by Ausubel et al. (1987). NI16 RNA is induced 5–10 fold within 15 minutes of SA or BTH induction and reaches a peak of approximately 50 fold induction within 2 hours of SA treatment and 25 fold induction with BTH treatment. The transcript remains highly induced up to 24 hours after SA and at least 48 hours after BTH treatment.

2. NI16 mRNA is Induced in Response to Pathogen Infection and is not Induced in NahG or nim1-4 Plants.

WS-O plants are infected with the avirulent pathogen *Pseudomonas syringae* p.v. tomato (P.s.t.) containing the avrRPM1 gene as described previously by Lawton et al. (1995). Three leaves of four week old plants are inoculated on one-half of the midrib with either buffer or P.s.t. and local and systemic tissue are harvested at 0, 2, 4, 6, 12, 24, 48, and 72 hours. NI16 is induced 5 fold within 4 hours in local tissue, and 6 hours in systemic tissue, and remains induced up to 72 hours after infection. In a separate experiment, WS-0, nim1-4, and NahG plants are inoculated with the same P.s.t. isolate and systemic tissue is harvested after 48 hours. nim1-4 plants are compromised in their ability to respond to pathogens as measured by their accumulation of PR-1 in response to chemical induction and pathogen treatment and their susceptibility to pathogens despite treatment with the chemical inducer 2,6-dichloroisonicotinic acid (Ryals et al., 1997). NahG plants express the bacterial salicylate hydroxylase (nahG) gene and are unable to accumulate salicylic acid (Gaffney et al. (1993) and Delaney et al. (1994). In wild type WS-O plants, NI16 is induced approximately 4 fold following P.s.t. inoculation but is not induced in NahG plants and is induced only slightly in nim1-4 plants. In another experiment nim1-4 plants are unable to accumulate NI16 transcript after 2 and 24 hours of BTH treatment. It can be concluded from these experiments that salicylic acid and a functional NIM1 protein are necessary for induction of NI16 in response to pathogens.

Example 3

Genomic Cloning of NI16 and Associated Promoter Sequence

A genomic copy of NI16 is cloned into the vector pBluescript from a Lambda ZapII library (Stratagene) according to the manufacturer's protocols. Two separate clones are obtained from the library. Clone 4-1 contains 3.1 kb of sequence upstream of NI16 and the coding region of NI16 up to the internal EcoRI site (see, SEQ ID NO:1). A second clone, 5-1, contains sequence 3' to the EcoRI site and 3.1 kb of sequence downstream of NI16. An intact genomic clone is obtained by first deleting a 1.87 kb BglII/BamHI fragment from clone 4-1 then ligating a 350 bp EcoRI/EcoRV fragment from clone 5-1 into the remaining EcoRI and EcoRV sites of clone 4-1. The genomic clones are sequenced, producing the NI16 genomic sequence shown as SEQ ID NO:3. Promoter elements are present in the 5' upstream region adjacent to the NI16 genomic coding region (see, SEQ ID NO:3). *E. coli* strain DH5α containing plasmid pRC25 (approximately 1.9 kb BglII/EcoRV genomic NI16 fragment in pBluescript) has been deposited with the NRRL on Jan. 7, 2000, and assigned accession number NRRL B-30239.

Example 4

Transgenic Expression of NI16 Results in Constitutive PR-1 Expression

A NI16 construct is made in binary vector pBAR35S (obtained from Jeff Dangl, UNC-Chapel Hill). First a full-length clone is obtained by cloning the 5'sequence of NI16 (obtained by 5' RACE and cloned into AT vector pCR2.1) into the EcoRI site of the original pJG4-5 clone as an EcoRI fragment. Then the entire coding region of NI16 is PCR cloned back into pCR2.1 with the primers 16F and 16 R (Table 1). The resulting plasmid is cut with XbaI and SacI for cloning into pBAR35S. The clone is transformed into *Agrobacterium* strain GV3101 (Koncz and Schell, 1986). WS-O and nim1-4 plants are transformed using standard procedures and the resulting T1 seed is selected by spraying with a 60 μg/ml solution of BASTA every two days for 6 days after germination. BASTA resistant plants are analyzed for levels of NI16 and PR-1 RNA after 4 weeks.

4 WS-O plants expressing NI16 above wild type levels are recovered. All have elevated levels of PR-1 RNA as detected on Northern blots. All 4 plants are taken to the T3 generations. Quantitative Northerns are done on two of the T3 lines, one with a relatively low level of NI16 RNA (1-1B) and one with a high level of NI16 RNA (2-1B). Northerns are hybridized with NI16 and PR-1 probes. Measurements are taken with a Molecular Dynamics Phosphoimager, which directly measures counts per unit area. The amount of PR-1 RNA correlates directly with the amount of NI16 RNA, i.e., the highest expressers of NI16 have the highest levels of PR-1. (Table 2). BTH applications at rates lower than that normally used to provide protection to *Peronospora* parasitica do not significantly increase the amount of NI16 RNA in the transgenic lines. PR-1 levels are induced at the same rate in the two NI16 lines as the WS-O control, however steady state PR-1 levels are higher, especially at 0 and 10 μm BTH. NI16 may therefore be necessary for the SAR response, and overexpression of NI16 may activate a subset of the response. PR-1 is also elevated in nahG, nim1-1 and nim1-4 plants overexpressing NI16. Out of 34 nim1-1 T1 plants containing the 35S-NI16 construct, 22 have elevated levels of PR-1. Similarly, 18/26 nim1-4 and 20/27 nahG primary transformants have elevated PR-1 levels. In each case, high NI16 expression is correlated with high PR-1 levels. This is significant because nim1 and nahG plants are normally deficient in their ability to induce PR1 in response to pathogens. Furthermore, this provides evidence that overexpression of NI16 can at least partially compensate for the absence of SA and a functional NIM protein in plants.

Example 5

Homologues of NI16 Cloned by PCR from Potato and Tomato

Homologues of NI16 from potato and tomato are cloned using the Marathon cDNA amplification kit. cDNA is made from potato and tomato polyA RNA and linkers are ligated at both ends according to the manufacturer's instructions. Degenerate primers are designed by comparing the *Arabidopsis* NI6 sequence with the tobacco G8-1 sequence (Horvath et al., 1998). The primers NI16 degR1 (SEQ ID NO:20) and NI16degF1 (SEQ ID NO:21), in combination with linker primers provided by Clonetech, are then used to amplify the 5' and 3' ends of the cDNAs. PCR products are then cloned using the TOPO-TA cloning kit from Invitrogen and sequenced. The entire potato cDNA (SEQ ID NO:4) and the 3'end of the tomato cDNA (SEQ ID NO:6) are recovered. Table 3 below shows a sequence alignment of the *Arabidopsis*, potato, and tomato clones, in addition to the polypeptide sequence encoded by the tobacco G8-1 gene and two soybean EST's (AI495102 and AI461039) identified by BLAST homology. All of the cDNA's encode small proteins (<122 amino acids) with a 22 amino acid core motif (bold) that is 45% identical and 82% similar among the 6 sequences.

TABLE 1

Primers Used In NIM1 and NI16 Cloning

| Primer Name | Sequence | SEQ ID NO: |
|---|---|---|
| NIM5'RI | ggaacgaattcatggacaccaccattg | SEQ ID NO:11 |
| NIM3'SalI | aaaaaagtcgactaagagcaagagtc | SEQ ID NO:12 |
| NIMtrunc3'NcoI | cgatctccatggcagcttgtcc | SEQ ID NO:13 |
| NIMloop5'RI | gaaccgaattcatgatcgca | SEQ ID NO:14 |
| 16GSP1 | ttccggtttacagttcagat | SEQ ID NO:15 |
| 16GSP2 | gacccgattaataatctcatcg | SEQ ID NO:16 |
| 16GSP3 | caccatttctggttggaggt | SEQ ID NO:17 |
| 16F | acgacgccgttaacattttc | SEQ ID NO:18 |
| 16R | gaaggggaaaaacatgaagga | SEQ ID NO:19 |
| NI16 DegF | cggaggnngaggtngaygagttyttc* | SEQ ID NO:20 |
| NI16 DegR | gaaraactcrtcnacctcnnccctccg* | SEQ ID NO:21 |

*n = a, c, t, or g; y = c or t; r = a or g

TABLE 2

Relative levels of NI16 and PR-1 in wild type *Arabidopsis* and two NI16-overexpressing lines 24 hours after induction with 0, 10 or 100 μm BTH.

| Genotype | BTH conc. (μm) | NI16 level | PR-1 level |
|---|---|---|---|
| WS | 0 | 1 | 1 |
|  | 10 | 10 | 30 |
|  | 100 | 90 | 90 |
| 1-1B | 0 | 760 | 3.5 |
|  | 10 | 1400 | 30 |
|  | 100 | 1480 | 120 |
| 2-1B | 0 | 11000 | 50 |
|  | 10 | 14000 | 70 |
|  | 100 | 12000 | 140 |

TABLE 3

Alignment of NI16 Homologous Sequences

| | | |
|---|---|---|
| AI495102 | ---MEVEKRKNKRVMGEEEESERVKNKRLKGVEEEDGSDGVPTEEEVEEFFAILRRMRMA | 57 |
| AI461039 | -------------------------------------GGVPTEEEVEEFFAILRRMRVA | 22 |
| Potato | MLLMDGEKKRKRTAIG-------AGDRSKDEVEATVKEEEPPSEAEXDEFFAILRRMHVA | 53 |
| Tomato | ------------------------------------SEGEVDEFFAILRRMHMA | 18 |
| G8-1 | ---MDGEKKRKRTENGKANGGDRNRHERKSAANEHTAVSPPPSEAEVDEFFAILRRMHVA | 57 |
| NI16 | ---MNNSLKKEERVEED------NGKSDGNRGKPSTEVVRTVTEEEVDEFFKILRRVHVA | 51 |
| | :* * :*** ****:::* | |
| AI495102 | VKYFDDKGRGGRE-WREAL--------------------------------------- | 75 |
| AI461039 | VKYFDDKGSGGKE-WRKALETAELTVDHRHDVVAAEEDDKPRKKGGEVI--INEGFDLNA | 79 |
| Potato | VKYLQRNAQIRPE-NLNAS-------PA-----GANGVAAGRKRERGIV--RKGDLDLNT | 98 |
| Tomato | VKYLQRNAQIQPE-NVNAHGSKLTASPA-----GVNGDATGQKRERGIV--RKGDLDLNT | 70 |
| G8-1 | VRYLQESGQKR-------------------------VVP-----------KGDLDLNT | 79 |
| NI16 | TRTVAKVNGGVAEGELPSKKRKRSQNLGLRNSLDCNGVRDGEFDEINRVGLQGLGLDLNC | 111 |
| | .: . | *** |
| AI495102 | ----------- | (SEQ ID NO:8) |
| AI461039 | VAPEAAEGGGA | 90 (SEQ ID NO:9) |
| Potato | LPDGGD----- | 104 (SEQ ID NO:5) |
| Tomato | LPDCGDT---- | 77 (SEQ ID NO:7) |
| G8-1 | LPGNGD----- | 85 (SEQ ID NO:10) |
| NI16 | KPEPDSVSLSL | 122 (SEQ ID NO:2) |

Example 6

Isolation of the NIM1 Interactor, NI19

In addition to the NI16 cDNA clone, the NI19 clone may also be isolated in the two-hybrid screen described in Example 1. A full-length clone is found be blasting the NI19 cDNA clone against the genbank database. A Bacterial Artificial Chromosome (BAC) in genbank (#F14J9) matches the sequence from bases 19726–19439. Additional flanking sequence (bases 19726–20000) is translated using GCG seqweb. An open reading frame is found between bases 19897–19513 that gives a predicted protein of 112 amino acids. The full-length *Arabidopsis* NI19 genomic sequence is shown as SEQ ID NO:22, and the encoded 112-amino acid protein sequence is shown as SEQ ID NO:23. Nucleotides 127–413 of SEQ ID NO:22 represent the original cDNA clone isolated in the NIM1 two-hybrid screen.

II. Expression of the Gene Sequences of the Invention in Plants

The NIM1 interactor of the present invention, NI16, can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgt11, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the NIM1 interactor increases SAR gene (e.g., PR-1) expression in the transgenic plants.

Example 7

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Callis et al., J. Biol. Chem. 265:12486–12493 (1990) and Norris et al., Plant Mol. Biol. 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761 ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761 ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the Arabidopsis PR-1 promoter described in Lebel et al., Plant J. 16:223–233 (1998) may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1 a promoter is cleaved from plasmid pCIB 1004 (for construction, see example 21 of EP 0 332 104, which is hereby incorporated by reference) and transferred to plasmid pCGN1761ENX (Uknes et al., Plant Cell 4: 645–656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from Aspergillus nidulans (Caddick et al. (1998) Nat. Biotechnol 16:177–180). In A. nidulans, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) Nat. Biotechnol 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) The Plant Journal 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) Science 231: 699–704) fused to the transactivating domain of the herpes viral protein VP16 (Triezenberg et al. (1988) Genes Devel. 2: 718–729) fused to the hormone-binding domain of the rat glucocorticoid receptor (Picard et al. (1988) Cell 54: 1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103–106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon Asparagus officinalis, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126–6130 (1989)); potyvirus leaders, for example, TEV leader (Tobacco Etch Virus) (Allison et al., 1986); MDMV leader (Maize Dwarf Mosaic Virus); *Virology* 154:9–20); human immunoglobulin heavy-chain binding protein (BiP) leader, (Macejak, D. G., and Sarnow, P., *Nature* 353: 90–94 (1991); untranslated leader from the coat protein mRNA of alfalfa mosaic virus (AMV RNA 4), (Jobling, S. A., and Gehrke, L., *Nature* 325:622–625 (1987); tobacco mosaic virus leader (TMV), (Gallie, D. R. et al., *Molecular Biology of RNA, pages* 237–256 (1989); and Maize Chlorotic Mottle Virus leader (MCMV) (Lommel, S. A. et al., *Virology* 81:382–385 (1991). See also, Della-Cioppa et al., *Plant Physiology* 84:965–968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., *Plant Cell* 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) *Plant Mol Biol* 23: 995–1003; Green (2000) *Trends Biochem Sci* 25: 59–63).

4. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. *J. Biol. Chem.* 263: 15104–15109 (1988)). These signal sequences can be fused to heterologous gene products to effect the import of heterologous products into the chloroplast (van den Broeck, et al. *Nature* 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al.

Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 8

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

a. pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces* viridochromogenes is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 9

Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and *Indica*-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using *Agrobacterium* has also been described. See, WO 94/00977 and U.S. Pat. No. 5,591,616, both of which are incorporated herein by reference.

3. Transformation of Plastids

Seeds of *Nicotiana tabacum* c.v. 'Xanthi nc' are germinated seven per plate in a 1" circular array on T agar medium and bombarded 12–14 days after sowing with 1 µm tungsten particles (M10, Biorad, Hercules, Calif.) coated with DNA from plasmids pPH143 and pPH145 essentially as described (Svab, Z. and Maliga, P. (1993) PNAS 90, 913–917). Bombarded seedlings are incubated on T medium for two days after which leaves are excised and placed abaxial side up in bright light (350–500 µmol photons/m$^2$/s) on plates of RMOP medium (Svab, Z., Hajdukiewicz, P. and Maliga, P. (1990) PNAS 87, 8526–8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

III. Breeding and Seed Production

Example 10

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 11

Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

IV. Disease Resistance Evaluation

Disease resistance evaluation is performed by methods known in the art. See, Uknes et al. (1993); Görlach et al. (1996); Alexander et al. (1993). For example, several representative disease resistance assays are described below.

Example 12

*Phytophthora parasitica* (Black Shank) Resistance Assay

Assays for resistance to *Phytophthora parasitica*, the causative organism of black shank, are performed on six-week-old plants grown as described in Alexander et al. (1993). Plants are watered, allowed to drain well, and then inoculated by applying 10 ml of a sporangium suspension (300 sporangia/ml) to the soil. Inoculated plants are kept in a greenhouse maintained at 23–25° C. day temperature, and 20–22° C. night temperature. The wilt index used for the assay is as follows: 0=no symptoms; 1=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

Example 13

*Pseudomonas syringae* Resistance Assay

*Pseudomonas syringae* pv. tabaci strain #551 is injected into the two lower leaves of several 6–7-week-old plants at a concentration of $10^6$ or $3 \times 10^6$ per ml in $H_2O$. Six individual plants are evaluated at each time point. *Pseudomonas tabaci* infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

Example 14

*Cercospora nicotianae* Resistance Assay

A spore suspension of *Cercospora nicotianae* (ATCC #18366) (100,000–150,000 spores per ml) is sprayed to imminent run-off onto the surface of the leaves. The plants are maintained in 100% humidity for five days. Thereafter the plants are misted with water 5–10 times per day. Six individual plants are evaluated at each time point. *Cercospora nicotianae* is rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

Example 15

*Peronospora parasitica* Resistance Assay

Assays for resistance to *Peronospora parasitica* are performed on plants as described in Uknes et al, (1993). Plants are inoculated with a compatible isolate of *P. parasitica* by spraying with a conidial suspension (approximately $5 \times 10^4$ spores per milliliter). Inoculated plants are incubated under humid conditions at 17° C. in a growth chamber with a 14-hr day/10-hr night cycle. Plants are examined at 3–14 days, preferably 7–12 days, after inoculation for the presence of conidiophores. In addition, several plants from each treatment are randomly selected and stained with lactophenol-trypan blue (Keogh et al., 1980) for microscopic examination.

The above disclosed embodiments are illustrative. This disclosure of the invention will place one skilled in the art in possession of many variations of the invention. All such obvious and foreseeable variations are intended to be encompassed by the claims.

REFERENCES

The references cited herein are indicative of the current state of the art. Each of the following is incorporated by reference into the instant disclosure.

U.S. Pat. No. 4,940,935
U.S. Pat. No. 4,945,050
U.S. Pat. No. 5,036,006
U.S. Pat. No. 5,100,792
U.S. Pat. No. 5,188,642
U.S. Pat. No. 5,523,311
U.S. Pat. No. 5,591,616
U.S. Pat. No. 5,614,395
U.S. Pat. No. 5,639,949
U.S. Pat. No. 5,792,904
EP 0 292 435
EP 0 332 104
EP 0 332 581
EP 0 342 926
EP 0 392 225
EP 0 452 269
International PCT Application WO 93/07278
International PCT Application WO 93/21335
International PCT Application WO 94/00977
International PCT Application WO 94/13822
International PCT Application WO 94/16077
International PCT Application WO 97/49822
International PCT Application WO 98/03536
International PCT Application WO 98/06748
International PCT Application WO 98/26082
International PCT Application WO 98/29537
Alexander et al., *Proc. Natl. Acad. Sci. USA* 90: 7327–7331 (1993)
Aoyama and Chua, *The Plant Journal* 11: 605–612 (1997)
Ausubel, F. M. et al., *Current Protocols in Molecular Biology*, pub. by Greene Publishing Assoc. and Wiley-Interscience (1987)
Bartlett et al., In: Edelmann et al. (Eds.) Methods in Chloroplast Molecular Biology, Elsevier 1081–1091 (1982)
Bevan et al., *Nature* 304:184–187 (1983)
Bevan, *Nucl. Acids Res.* (1984)
Bi et al., *Plant J.* 8: 235–245 (1995)
Binet et al. *Plant Science* 79: 87–94 (1991)
Blochinger & Diggelmann, *Mol Cell. Biol.* 4: 2929–2931
Bourouis et al., *EMBO J.* 2(7): 1099–1104 (1983)
Boutry et al., *Nature* 328:340–342 (1987)
Caddick et al., *Nat. Biotechnol* 16:177–180 (1998)
Callis et al., *Genes Develop.* 1: 1183–1200 (1987)
Cameron et al., *Plant J.* 5: 715–725 (1994)
Cao et al., *Plant Cell* 6, 1583–1592 (1994)
Cao et al., *Cell* 88: 57–63 (1997)
Casas et al., *Proc. Natl. Acad. Sci. USA* 90: 11212–11216 (1993)
Century et al., *Proc. Natl. Acad. Sci. USA* 92: 6597–6601 (1995)
Chibbar et al., *Plant Cell Rep.* 12: 506–509 (1993)
Chrispeels, *Ann. Rev. Plant Physiol. Plant Mol. Biol.* 42: 21–53 (1991)
Christou et al., *Plant Physiol.* 87:671–674 (1988)
Christou et al., *Biotechnology* 9: 957–962 (1991)
Christensen et al., *Plant Molec. Biol.* 12: 619–632 (1989)
Comai et al., *J. Biol. Chem.* 263: 15104–15109 (1988)
Crossway et al., *BioTechniques* 4:320–334 (1986)
Datta et al., *Biotechnology* 8: 736–740 (1990)
de Framond, *FEBS* 290: 103–106 (1991)
Delaney et al., *Science* 266: 1247–1250 (1994)
Delaney et al., *Proc. Natl. Acad. Sci. USA* 92: 6602–6606 (1995)
Dempsey and Klessig, *Bulletin de L'Institut Pasteur* 93: 167–186 (1995)
Dietrich et al., *Cell* 77: 565–577 (1994)
Fields and Song, *Nature* 340:245–247 (1989)
Firek et al., *Plant Molec. Biol.* 22: 129–142 (1993)
Fromm et al., *Biotechnology* 8: 833–839 (1990)
Gaffney et al., *Science* 261: 754–756 (1993)
Gallie et al., *Nucl. Acids Res.* 15: 8693–8711 (1987)
Glazebrook et al., *Genetics* 143: 973–982 (1996)
Goldsbrough et al., *Plant Journal* 3: 563–571 (1993)
Gordon-Kamm et al., *Plant Cell* 2: 603–618 (1990)

Gordon-Kamm et al, in "Transgenic Plants", vol. 2, pp. 21–33, pub. by Academic Press (1993)
Gölach et al., *Plant Cell* 8: 629–643 (1996)
Greenberg et al., *Cell* 77: 551–563 (1994)
Gritz et al., *Gene* 25: 179–188 (1983)
Gyuris et al., *Cell* 75: 791–803 (1993)
Hayashimoto et al., *Plant Physiol.* 93: 857–863 (1990)
Hill et al., *Euphytica* 85:119–123 (1995)
Hinchee et al., *Biotechnology* 6:915–921 (1988)
Höfgen & Willmitzer, *Nucl. Acids Res.* 16: 9877 (1988)
Horvath et al., *Mol. Plant-Microbe Interact.* 11: 895–905 (1996)
Hudspeth & Grula, *Plant Molec. Biol* 12: 579–589 (1989)
Hunt and Ryals, *Crit. Rev. in Plant Sci.* 15: 583–606 (1996)
Innis et al., *PCR Protocols, a Guide to Methods and Applications* eds., Academic Press (1990)
Ishida et al., *Nature Biotechnology* 14: 745–750 (1996)
Jahne et al., *Theor. Appl. Genet.* 89: 525–533 (1994)
Keegan et al., *Science* 231: 699–704 (1986)
Keogh et al., *Trans. Br. Mycol. Soc.* 74: 329–333 (1980)
Klein et al., *Nature* 327: 70–73 (1987)
Klein et al., *Proc. Natl. Acad. Sci. USA* 85:4305–4309 (1988)
Klein et al., *Bio/Technology* 6:559–563 (1988)
Klein et al., *Plant Physiol.* 91:440–444 (1988)
Koncz and Schell, *Mol. Gen. Genet.* 204: 383–396 (1986)
Koziel et al., *Biotechnology* 11: 194–200 (1993)
Koziel et al., *Annals of the New York Academy of Sciences* 792:164–171 (1996)
Lawton et al., "The molecular biology of systemic aquired resistance" in *Mechanisms of Defence Responses in Plants*, B. Fritig and M. Legrand, eds (Dordrecht, The Netherlands: Kluwer Academic Publishers), pp. 422–432 (1993)
Lawton et al., *Mol. Plant-Microbe Interact.* 6: 863–870 (1995)
Lawton et al., *Plant J.* 10: 71–82 (1996)
Logemann et al., *Plant Cell* 1: 151–158 (1989)
Maher et al., *Proc. Natl. Acad. Sci. USA* 91: 7802–7806 (1994)
Mauch-Mani and Slusarenko, *Mol. Plant-Microbe Interact.* 7: 378–383 (1994)
Mauch-Mani and Slusarenko, *Plant Cell* 8: 203–212 (1996)
Mayo O., *The Theory of Plant Breeding*, Second Edition, Clarendon Press, Oxford (1987)
Mazur et al., *Plant Physiol.* 85: 1110 (1987)
McBride et al., *Plant Molecular Biology* 14: 266–276 (1990)
McCabe et al., *Biotechnology* 6:923–926 (1988)
McElroy et al., *Plant Cell* 2: 163–171 (1990)
McElroy et al., *Mol. Gen. Genet.* 231: 150–160 (1991)
Messing & Vierra, *Gene* 19: 259–268 (1982)
Murashiga & Skoog, *Physiologia Plantarum* 15: 473–497 (1962)
Nehra et al., *The Plant Journal* 5: 285–297 (1994)
Neuhaus et al., *Proc. Natl. Acad. Sci. USA* 88: 10362–10366 (1991)
Norris et al., *Plant Mol. Biol.* 21: 895–906 (1993)
Pallas et al., *Plant J.* 10: 281–293 (1996)
Parker et al., *Plant Cell* 8: 2033–2046 (1996)
Paszkowski et al., *EMBO J.* 3: 2717–2722 (1984)
Payne et al., *Plant Mol. Biol.* 11:89–94 (1988)
Picard et al., *Cell* 54: 1073–1080 (1988)
Potrykus et al., *Mol. Gen. Genet.* 199: 169–177 (1985)
Reich et al., *Biotechnology* 4: 1001–1004 (1986)
Riggs et al, *Proc. Natl. Acad. Sci. USA* 83:5602–5606 (1986)
Rogers et al., *Proc. Natl. Acad. Sci. USA* 82: 6512–6516 (1985)
Rohrmeier & Lehle, *Plant Molec. Biol.* 22: 783–792 (1993)
Rothstein et al., *Gene* 53: 153–161 (1987)
Ryals et al., *Plant Cell* 8: 1809–1819 (1996)
Ryals et al., *Plant Cell* 9: 425439 (1997)
Sambrook et al., *Molecular Cloning*, eds., Cold Spring Harbor Laboratory Press (1989)
Sanford et al., *Particulate Science and Technology* 5:27–37 (1987)
Schmidhauser & Helinski, *J. Bacteriol.* 164: 446–455 (1985)
Schocher et al., *Biotechnology* 4: 1093–1096 (1986)
Shimamoto et al., *Nature* 338: 274–277 (1989)
Shinshi et al., *Plant Molec. Biol.* 14: 357–368 (1990)
Shulaev et al., *Plant Cell* 7: 1691–1701 (1995)
Silhavy, et al., *Experiments with Gene Fusions*, eds., Cold Spring Harbor Laboratory Press (1984)
Singh, D. P., *Breeding for Resistance to Diseases and Insect Pests*, Springer-Verlag, NY (1986)
Skuzeski et al., *Plant Molec. Biol.* 15: 65–79 (1990)
Somers et al., *Bio/Technology* 10: 1589–1594 (1992)
Spencer et al., *Theor. Appl. Genet.* 79: 625–631 (1990)
Stanford et al., *Mol Gen. Genet.* 215: 200–208 (1989)
Svab et al., *Proc. Natl. Acad. Sci. USA* 87:8526–8530 (1990)
Taylor et al., *Plant Cell Rep.* 12: 491–495 (1993)
Terzaghi and Cashmore, *Annu. Rev. Plant Physiol. Plant Mol. Biol.* 46:445–474 (1995)
Thompson et al. *EMBO J.* 6: 2519–2523 (1987)
Torbert et al., *Plant Cell Reports* 14: 635–640 (1995)
Triezenberg et al., *Genes Devel.* 2: 718–729 (1988)
Uknes et al., *Plant Cell* 4: 645–656 (1992)
Uknes et al. *Plant Cell* 5: 159–169 (1993)
Uknes et al., *Molecular Plant Microbe Interactions* 6: 680–685 (1993)
Uknes et al., *Mol. Plant-Microbe Interact.* 6: 692–698 (1993)
Umbeck et al., *Bio/Technology* 5: 263–266 (1987)
Unger et al., *Plant Molec. Biol.* 13: 411–418 (1989)
van den Broeck, et al., *Nature* 313: 358–363 (1985)
Vasil et al., *Biotechnology* 10: 667–674 (1992)
Vasil et al., *Biotechnology* 11: 1553–1558 (1993)
Vernooij et al., *Plant Cell* 6: 959–965 (1994)
Vernooij et al., *Mol. Plant-Microbe Interact.* 8: 228–234 (1995)
Von Heijne et al., *Plant Mol. Biol. Rep.* 9:104–126 (1991)
Vorst et al., *Gene* 65: 59 (1988)
Wan et al., *Plant Physiol.* 104: 37–48 (1994)
Ward et al., *Plant Cell* 3: 1085–1094 (1991)
Warner et al., *Plant J.* 3: 191–201 (1993)
Wasmann et al., *Mol. Gen. Genet.* 205: 446–453 (1986)
Weeks et al., *Plant Physiol.* 102: 1077–1084 (1993)
Weissinger et al., *Annual Rev. Genet.* 22:421–477 (1988)
Welsh J. R., *Fundamentals of Plant Genetics and Breeding*, John Wiley & Sons, NY (1981)
Weymann et al., *Plant Cell* 7: 2013–2022 (1995)
White et al., *Nucl. Acids Res.* 18: 1062 (1990)
Wood D. R. (Ed.) *Crop Breeding*, American Society of Agronomy Madison, Wis. (1983)
Wricke and Weber, *Quantitative Genetics and Selection Plant Breeding*, Walter de Gruyter and Co., Berlin (1986)
Xu et al., *Plant Molec. Biol.* 22: 573–588 (1993)
Zhang et al., *Plant Cell Rep.* 7: 379–384 (1988)

What is claimed is:

1. An isolated nucleic acid promoter comprising nucleotides 1 to 862 of SEQ ID NO: 3.

2. A chimeric gene comprising the promoter according to claim 1 operatively linked to a coding sequence of interest.

3. A recombinant vector comprising the chimeric gene of claim 2.

4. A transgenic host cell comprising the chimeric gene of claim 2.

5. A transgenic host cell according to claim 4, which is a transgenic plant cell.

6. A transgenic plant comprising the recombinant vector of claim 3.

7. Transgenic seed from the transgenic plant according to claim 5, wherein the seed comprises the chimeric gene.

* * * * *

SEQUENCE LISTING

<160> NUMBER OF SEQ ID NOS: 23

<210> SEQ ID NO 1
<211> LENGTH: 509
<212> TYPE: DNA
<213> ORGANISM: Arabidopsis thaliana
<220> FEATURE:
<221> NAME/KEY: CDS
<222> LOCATION: (68)..(433)
<223> OTHER INFORMATION: gene product NI16
<220> FEATURE:
<221> NAME/KEY: misc_feature
<222> LOCATION: (142)..(147)
<223> OTHER INFORMATION: SalI site
<220> FEATURE:
<221> NAME/KEY: misc_feature
<222> LOCATION: (344)..(349)
<223> OTHER INFORMATION: EcoRI site

<400> SEQUENCE: 1

```
aaaatcagca aataaacttt tcttgactaa gcttaaacga cgccgttaac attttcttct        60 ggctaac atg aac aac tct ttg aag aaa gaa gaa cgc gta gaa gaa gat        109
        Met Asn Asn Ser Leu Lys Lys Glu Glu Arg Val Glu Glu Asp
          1               5                  10 aac gga aaa tct gac ggt aac aga ggg aaa ccg tcg acg gaa gtt gtt        157
Asn Gly Lys Ser Asp Gly Asn Arg Gly Lys Pro Ser Thr Glu Val Val
 15                  20                  25                  30 cgg acg gta acg gag gaa gag gtg gat gag ttt ttc aag ata tta cgg        205
Arg Thr Val Thr Glu Glu Glu Val Asp Glu Phe Phe Lys Ile Leu Arg
                 35                  40                  45 aga gta cac gtg gcg aca cga acg gtt gcg aaa gtt aac ggc ggt gtt        253
Arg Val His Val Ala Thr Arg Thr Val Ala Lys Val Asn Gly Gly Val
             50                  55                  60 gct gag gga gag tta ccg tct aag aag agg aaa cgg agt cag aat ctt        301
Ala Glu Gly Glu Leu Pro Ser Lys Lys Arg Lys Arg Ser Gln Asn Leu
         65                  70                  75 ggg ttg aga aac tcg ttg gat tgt aac ggc gtt cga gac gga gaa ttc        349
Gly Leu Arg Asn Ser Leu Asp Cys Asn Gly Val Arg Asp Gly Glu Phe
     80                  85                  90 gat gag att aat cgg gtc ggg tta cag ggt ttg ggt ttg gat ctg aac        397
Asp Glu Ile Asn Arg Val Gly Leu Gln Gly Leu Gly Leu Asp Leu Asn
 95                 100                 105                 110 tgt aaa ccg gaa cca gac agc gtt agt tta tcg ttg tagacttgta            443
Cys Lys Pro Glu Pro Asp Ser Val Ser Leu Ser Leu
                115                 120 gtccttcatg tttttcccct tcttacaata atcattttt ttttaactac aatactttg       503 aaaaaa                                                               509
```

<210> SEQ ID NO 2
<211> LENGTH: 122
<212> TYPE: PRT
<213> ORGANISM: Arabidopsis thaliana

<400> SEQUENCE: 2

```
Met Asn Asn Ser Leu Lys Lys Glu Glu Arg Val Glu Glu Asp Asn Gly
  1               5                  10                  15

Lys Ser Asp Gly Asn Arg Gly Lys Pro Ser Thr Glu Val Val Arg Thr
             20                  25                  30

Val Thr Glu Glu Glu Val Asp Glu Phe Phe Lys Ile Leu Arg Arg Val
         35                  40                  45
```

-continued

```
His Val Ala Thr Arg Thr Val Ala Lys Val Asn Gly Gly Val Ala Glu
 50                  55                  60

Gly Glu Leu Pro Ser Lys Lys Arg Lys Arg Ser Gln Asn Leu Gly Leu
 65                  70                  75                  80

Arg Asn Ser Leu Asp Cys Asn Gly Val Arg Asp Gly Glu Phe Asp Glu
                 85                  90                  95

Ile Asn Arg Val Gly Leu Gln Gly Leu Gly Leu Asp Leu Asn Cys Lys
            100                 105                 110

Pro Glu Pro Asp Ser Val Ser Leu Ser Leu
            115                 120
```

<210> SEQ ID NO 3
<211> LENGTH: 1700
<212> TYPE: DNA
<213> ORGANISM: Arabidopsis thaliana
<220> FEATURE:
<221> NAME/KEY: misc_feature
<222> LOCATION: (365)..(374)
<223> OTHER INFORMATION: TCA1 motif
<220> FEATURE:
<221> NAME/KEY: misc_feature
<222> LOCATION: (426)..(435)
<223> OTHER INFORMATION: TCA1 motif
<220> FEATURE:
<221> NAME/KEY: misc_feature
<222> LOCATION: (609)..(614)
<223> OTHER INFORMATION: MYCATR22 element
<220> FEATURE:
<221> NAME/KEY: misc_feature
<222> LOCATION: (646)..(665)
<223> OTHER INFORMATION: CAMV AS1 salicylic acid response element
<220> FEATURE:
<221> NAME/KEY: misc_feature
<222> LOCATION: (707)..(712)
<223> OTHER INFORMATION: PAL BOX
<220> FEATURE:
<221> NAME/KEY: misc_feature
<222> LOCATION: (757)..(762)
<223> OTHER INFORMATION: HEXAMERAT 4 element
<220> FEATURE:
<221> NAME/KEY: misc_feature
<222> LOCATION: (863)..(1228)
<223> OTHER INFORMATION: NI16 genomic coding region

<400> SEQUENCE: 3

```
tgggttttta ttggataaca tgacaaatat ttatttattt catgagtttt tattggatag      60
catgacaaat attaatatat cagtgttaat aacatgtttt gttcttaaaa tacatgcatt     120
ttaaaatcag acatttgttt taaaatcaaa tctaatctct tatatcacaa cgacattgac     180
ggaaaattca ggtaaaaaga gaaataaag aatgagagat agagagattt ctatggaaaa      240
agaaagagag aacatgtagg tgaacaaaat aaagagatat gatgatatat tttatgagag     300
gtggtgaaga ttattttagg agagggagag agaaatagaa aaagaaaatg acatggtgaa     360
tctgaagaag atgaattgtg ttaaagatga agagagaaag agaactccat ggctaaagtc     420
tcgtaaagaa gatgaaaaag aaacaaaaga aggaagaaga aagagaaagg ctaaaataga     480
ctaactattg ccaaaatttc tgtagccgac aaatactatt tggtccaagg ttattttgtg     540
tattcttttg aagtcaaaag ttatttctta catatactct aaaaatatag ccgataccaa     600
tttttccaca catggacttc ctttattcca aaagtcaata aagtgtgacg tcatgatact     660
tacgctttaa aacatcgcat gatgatgtca ttagcatcaa tctccaccgt ccaatttatt     720
tagttgttga caatatcgac cgtctaagtt ccacaccgac ggctataaga gtttcattat     780 aaatttagc aaaataaaat cagcaaataa ttttttcttg actaagctta aacgacgccg      840
```

```
ttaacatttt cttctggcta acatgaacaa ctctttgaag aaagaagaac gcgtagaaga      900
agataacgga aaatctgacg gtaacagagg gaaaccgtcg acggaagttg ttcggacggt      960
aacggaggaa gaggtggatg agttttcaa gatattacgg agagtacacg tgcgacacg       1020 aacggttgcg aaagttaacg gcggtgttgc tgagggagag ttaccgtcta agaagaggaa    1080
acggagtcag aatcttgggt tgagaaactc gttggattgt aacggcgttc gagacggaga    1140
attcgatgag attaatcggg tcgggttaca gggtttgggt ttggatctga actgtaaacc    1200
ggaaccagac agcgttagtt tatcgttgta gacttgtagt ccttcatgtt tttcccttc     1260 ttacaataat caatttttt ttaactacaa tacttttgaa aaaaatggta aagaagatt       1320 attaacatgt tatccaaatt tcagattctt cagttttatt ttatacgtca aaagagaagt   1380
tatatatttg caaaactaca agtcaaacaa aagctattta agcgtttgac gttcctaaac    1440
aacataaatt ttactaaaat caatgtttta aaaagtgtt gatggtaaag atatcaattg     1500
ggcctttgcc tggcccgttt agtaatattg cagagtaggt atgggcctgt ataagggagt   1560
ccaaaaaaag agcgggcatt gcgggttggg tgcgtttgga actttggatt gtggattagt    1620
catggtttat ctattaatgt ctgcggactt gtggacgacg cgcttgttct tcttcctctg    1680
tttacgactt acgaacatat                                                 1700

<210> SEQ ID NO 4
<211> LENGTH: 608
<212> TYPE: DNA
<213> ORGANISM: Solanum tuberosum
<220> FEATURE:
<221> NAME/KEY: CDS
<222> LOCATION: (124)..(438)

<400> SEQUENCE: 4
caggtaatac acacagaaaa cattgacata acagatcgaa tacacattat attatattaa      60
tgagagaata aagagaagta attgcactag cagtattgac aattaatcag ctagccggct     120 tga atg cta ctt atg gac gga gaa aag aag agg aag aga aca gca atc        168
    Met Leu Leu Met Asp Gly Glu Lys Lys Arg Lys Arg Thr Ala Ile
    1               5                   10                  15 ggc gcc gga gat cgg agt aag gat gag gta gaa gct act gtg aag gag       216
Gly Ala Gly Asp Arg Ser Lys Asp Glu Val Glu Ala Thr Val Lys Glu
            20                  25                  30 gag gag ccg ccg tca gag gcg gag gtt gac gag ttc ttc gcg atc tta       264
Glu Glu Pro Pro Ser Glu Ala Glu Val Asp Glu Phe Phe Ala Ile Leu
        35                  40                  45 cgg agg atg cat gtg gcg gtg aaa tat ctc cag aga aat gct cag att       312
Arg Arg Met His Val Ala Val Lys Tyr Leu Gln Arg Asn Ala Gln Ile
    50                  55                  60 cgg ccg gaa aac ctt aac gca tcg ccg gcc ggt gct aac ggt gtc gca       360
Arg Pro Glu Asn Leu Asn Ala Ser Pro Ala Gly Ala Asn Gly Val Ala
65                  70                  75 gct gga cgg aag aga gaa cgg gga atc gtg aga aaa ggt gat ttg gac       408
Ala Gly Arg Lys Arg Glu Arg Gly Ile Val Arg Lys Gly Asp Leu Asp
 80                  85                  90                  95 ctc aac act ctg ccg gac ggc gga gac taa ttaacgcagt ttaagcatag         458
Leu Asn Thr Leu Pro Asp Gly Gly Asp
                100                 105 gttaattaca taaatgcacc cttaattatc gtagattctt aagattgatc tgctgtacag    518
attaattaat taaagccttt ttttatatat atttctccgg taaacggttt gctctttgtg    578
attttcttta ataaatttaa tttattttat                                      608
```

```
<210> SEQ ID NO 5
<211> LENGTH: 104
<212> TYPE: PRT
<213> ORGANISM: Solanum tuberosum

<400> SEQUENCE: 5

Met Leu Leu Met Asp Gly Glu Lys Lys Arg Lys Arg Thr Ala Ile Gly
  1               5                  10                  15

Ala Gly Asp Arg Ser Lys Asp Glu Val Glu Ala Thr Val Lys Glu Glu
                 20                  25                  30

Glu Pro Pro Ser Glu Ala Glu Val Asp Glu Phe Phe Ala Ile Leu Arg
             35                  40                  45

Arg Met His Val Ala Val Lys Tyr Leu Gln Arg Asn Ala Gln Ile Arg
         50                  55                  60

Pro Glu Asn Leu Asn Ala Ser Pro Ala Gly Ala Asn Gly Val Ala Ala
 65                  70                  75                  80

Gly Arg Lys Arg Glu Arg Gly Ile Val Arg Lys Gly Asp Leu Asp Leu
                 85                  90                  95

Asn Thr Leu Pro Asp Gly Gly Asp
            100

<210> SEQ ID NO 6
<211> LENGTH: 349
<212> TYPE: DNA
<213> ORGANISM: Lycopersicon esculentum
<220> FEATURE:
<221> NAME/KEY: CDS
<222> LOCATION: (3)..(233)

<400> SEQUENCE: 6 ct tcg gag gga gag gtg gat gag ttt ttc gca att tta cgg agg atg      47
   Ser Glu Gly Glu Val Asp Glu Phe Phe Ala Ile Leu Arg Arg Met
     1               5                  10                  15 cac atg gcc gta aaa tat ctt cag aga aac gct cag att cag ccg gaa     95
His Met Ala Val Lys Tyr Leu Gln Arg Asn Ala Gln Ile Gln Pro Glu
             20                  25                  30 aac gtt aac gct cac ggc agc aag tta acc gca tcg ccg gcc ggt gtt    143
Asn Val Asn Ala His Gly Ser Lys Leu Thr Ala Ser Pro Ala Gly Val
         35                  40                  45 aac gga gat gca act gga cag aag aga gaa cgg gga atc gtg aga aaa    191
Asn Gly Asp Ala Thr Gly Gln Lys Arg Glu Arg Gly Ile Val Arg Lys
     50                  55                  60 ggt gat ttg gac ctc aac act ttg ccg gac tgc gga gac taa            233
Gly Asp Leu Asp Leu Asn Thr Leu Pro Asp Cys Gly Asp
 65                  70                  75 cgcagtttaa gcataggtta attacagaaa tgcacctta attatcgtag attcttaaga   293
ttgatctgct gtacaaatta attaaatgaa gcctttttt atatataaaa aaaaaa       349

<210> SEQ ID NO 7
<211> LENGTH: 76
<212> TYPE: PRT
<213> ORGANISM: Lycopersicon esculentum

<400> SEQUENCE: 7

Ser Glu Gly Glu Val Asp Glu Phe Phe Ala Ile Leu Arg Arg Met His
  1               5                  10                  15

Met Ala Val Lys Tyr Leu Gln Arg Asn Ala Gln Ile Gln Pro Glu Asn
                 20                  25                  30

Val Asn Ala His Gly Ser Lys Leu Thr Ala Ser Pro Ala Gly Val Asn
```

```
                35                  40                  45
Gly Asp Ala Thr Gly Gln Lys Arg Glu Arg Gly Ile Val Arg Lys Gly
        50                  55                  60
Asp Leu Asp Leu Asn Thr Leu Pro Asp Cys Gly Asp
65                  70                  75

<210> SEQ ID NO 8
<211> LENGTH: 75
<212> TYPE: PRT
<213> ORGANISM: Glycine max

<400> SEQUENCE: 8

Met Glu Val Glu Lys Arg Lys Asn Lys Arg Val Met Gly Glu Glu Glu
1               5                   10                  15
Glu Ser Glu Arg Val Lys Asn Lys Arg Leu Lys Gly Val Glu Glu Glu
                20                  25                  30
Asp Gly Ser Asp Gly Val Pro Thr Glu Glu Val Glu Glu Phe Phe
        35                  40                  45
Ala Ile Leu Arg Arg Met Arg Met Ala Val Lys Tyr Phe Asp Asp Lys
    50                  55                  60
Gly Arg Gly Gly Arg Glu Trp Arg Glu Ala Leu
65                  70                  75

<210> SEQ ID NO 9
<211> LENGTH: 90
<212> TYPE: PRT
<213> ORGANISM: Glycine max

<400> SEQUENCE: 9

Gly Gly Val Pro Thr Glu Glu Val Glu Glu Phe Phe Ala Ile Leu
1               5                   10                  15
Arg Arg Met Arg Val Ala Val Lys Tyr Phe Asp Asp Lys Gly Ser Gly
                20                  25                  30
Gly Lys Glu Trp Arg Lys Ala Leu Glu Thr Ala Glu Leu Thr Val Asp
        35                  40                  45
His Arg His Asp Val Val Ala Ala Glu Glu Asp Lys Pro Arg Lys
    50                  55                  60
Lys Gly Glu Val Ile Ile Asn Glu Gly Phe Asp Leu Asn Ala Val
65                  70                  75                  80
Ala Pro Glu Ala Ala Glu Gly Gly Gly Ala
                85                  90

<210> SEQ ID NO 10
<211> LENGTH: 85
<212> TYPE: PRT
<213> ORGANISM: Nicotiana tabacum

<400> SEQUENCE: 10

Met Asp Gly Glu Lys Lys Arg Lys Arg Thr Glu Asn Gly Lys Ala Asn
1               5                   10                  15
Gly Gly Asp Arg Asn Arg His Glu Arg Lys Ser Ala Ala Asn Glu His
                20                  25                  30
Thr Ala Val Ser Pro Pro Ser Glu Ala Glu Val Asp Glu Phe Phe
        35                  40                  45
Ala Ile Leu Arg Arg Met His Val Ala Val Arg Tyr Leu Gln Glu Ser
    50                  55                  60
Gly Gln Lys Arg Val Val Pro Lys Gly Asp Leu Asp Leu Asn Thr Leu
65                  70                  75                  80
```

```
Pro Gly Asn Gly Asp
              85

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer
      NIM5'RI

<400> SEQUENCE: 11
ggaacgaatt catggacacc accattg                                         27

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer
      NIM3'SalI

<400> SEQUENCE: 12
aaaaaagtcg actaagagca agagtc                                          26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer
      NIMtrunc3'NcoI

<400> SEQUENCE: 13
cgatctccat ggcagcttgt cc                                              22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer
      NIMloop5'RI

<400> SEQUENCE: 14
gaaccgaatt catgatcgca                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer
      16GSP1

<400> SEQUENCE: 15
ttccggttta cagttcagat                                                 20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer GSP2

<400> SEQUENCE: 16
```

-continued

```
gacccgatta ataatctcat cg                                             22
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer GSP3

<400> SEQUENCE: 17

```
caccatttct ggttggaggt                                                20
```

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer 16F

<400> SEQUENCE: 18

```
acgacgccgt taacattttc                                                20
```

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Primer 16R

<400> SEQUENCE: 19

```
gaagggaaa aacatgaagg a                                               21
```

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: PCR primer
      NI16-DegF
<220> FEATURE:
<221> NAME/KEY: misc_feature
<222> LOCATION: (1)..(26)
<223> OTHER INFORMATION: n = a, t, c, or g

<400> SEQUENCE: 20

```
cggaggnnga ggtngaygag ttyttc                                         26
```

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: PCR primer
     NI16-DegR
<220> FEATURE:
<221> NAME/KEY: misc_feature
<222> LOCATION: (1)..(27)
<223> OTHER INFORMATION: n = a, t, c, or g

<400> SEQUENCE: 21

```
gaaraactcr tcnacctcnn ccctccg                                        27
```

<210> SEQ ID NO 22
<211> LENGTH: 413
<212> TYPE: DNA
<213> ORGANISM: Arabidopsis thaliana
<220> FEATURE:
<221> NAME/KEY: CDS -continued

```
<222> LOCATION: (1)..(336)
<223> OTHER INFORMATION: NI19

<400> SEQUENCE: 22 atg gac aga gac aga aag agg gtg aaa atg gag aag gaa gat gac gaa      48
Met Asp Arg Asp Arg Lys Arg Val Lys Met Glu Lys Glu Asp Asp Glu
1               5                   10                  15 gaa gaa aag atg gag aag ttg tac aca gtg ctt aaa aac gca agg gaa      96
Glu Glu Lys Met Glu Lys Leu Tyr Thr Val Leu Lys Asn Ala Arg Glu
                20                  25                  30 atg cgg aaa tat gtc aac agc tcc atg gag aag aag aga cag gaa gaa     144
Met Arg Lys Tyr Val Asn Ser Ser Met Glu Lys Lys Arg Gln Glu Glu
            35                  40                  45 gaa gaa aga gca agg gtt cgt aga ttc cct tcg ttt cag cca gaa gat     192
Glu Glu Arg Ala Arg Val Arg Arg Phe Pro Ser Phe Gln Pro Glu Asp
        50                  55                  60 ttc att ttc atg aat aaa gca gag gcc aac aac att gaa aaa gca gct     240
Phe Ile Phe Met Asn Lys Ala Glu Ala Asn Asn Ile Glu Lys Ala Ala
65                  70                  75                  80 aat gag agc tct tca gca tcc aac gag tat gat ggc tct aag gaa aag     288
Asn Glu Ser Ser Ser Ala Ser Asn Glu Tyr Asp Gly Ser Lys Glu Lys
                85                  90                  95 caa gaa gga tct gag act aac gtt tgt tta gac ttg aat ctt tct ctg     336
Gln Glu Gly Ser Glu Thr Asn Val Cys Leu Asp Leu Asn Leu Ser Leu
                100                 105                 110 tagcatacat acatacaaga gacaaagagc tcttcagttt ctgtataagc aacaaagaat   396
gttagtaact acgtacc                                                  413

<210> SEQ ID NO 23
<211> LENGTH: 112
<212> TYPE: PRT
<213> ORGANISM: Arabidopsis thaliana

<400> SEQUENCE: 23

Met Asp Arg Asp Arg Lys Arg Val Lys Met Glu Lys Glu Asp Asp Glu
1               5                   10                  15

Glu Glu Lys Met Glu Lys Leu Tyr Thr Val Leu Lys Asn Ala Arg Glu
                20                  25                  30

Met Arg Lys Tyr Val Asn Ser Ser Met Glu Lys Lys Arg Gln Glu Glu
            35                  40                  45

Glu Glu Arg Ala Arg Val Arg Arg Phe Pro Ser Phe Gln Pro Glu Asp
        50                  55                  60

Phe Ile Phe Met Asn Lys Ala Glu Ala Asn Asn Ile Glu Lys Ala Ala
65                  70                  75                  80

Asn Glu Ser Ser Ser Ala Ser Asn Glu Tyr Asp Gly Ser Lys Glu Lys
                85                  90                  95

Gln Glu Gly Ser Glu Thr Asn Val Cys Leu Asp Leu Asn Leu Ser Leu
                100                 105                 110
```